United States Patent [19]

Quack et al.

[11] 4,150,216

[45] Apr. 17, 1979

[54] HAIR-TREATING AGENTS FROM BRANCHED, SULFO-GROUP CONTAINING COPOLYESTERS

[75] Inventors: Jochen M. Quack; Alwin Reng, both of Kelkheim; Friedrich Engelhardt; Karl Hintermeier, both of Frankfurt am Main, all of Fed. Rep. of Germany

[73] Assignee: Hoechst Aktiengesellschaft, Frankfurt am Main, Fed. Rep. of Germany

[21] Appl. No.: 817,054

[22] Filed: Jul. 19, 1977

[30] Foreign Application Priority Data

Jul. 24, 1976 [DE] Fed. Rep. of Germany ....... 2633418

[51] Int. Cl.² .............................................. C08G 63/68
[52] U.S. Cl. ...................... 528/290; 560/14; 560/151; 424/70; 424/71; 528/176; 528/291; 528/292; 528/293; 528/296
[58] Field of Search ................. 260/75 S; 560/14, 151

[56] References Cited

U.S. PATENT DOCUMENTS

| | | | |
|---|---|---|---|
| 3,018,272 | 1/1962 | Griffing et al. | 260/75 S |
| 3,033,824 | 5/1962 | Huffman | 260/75 S |
| 3,563,942 | 2/1971 | Heiberger | 260/29.2 |
| 3,594,412 | 7/1971 | Burkhardt | 560/14 X |
| 3,734,874 | 5/1973 | Kibler et al. | 260/29.2 E |
| 3,853,820 | 12/1974 | Vachon | 260/75 T |
| 3,882,185 | 5/1975 | Radlmann et al. | 260/75 S |
| 4,048,149 | 9/1977 | Fritz et al. | 560/14 X |

*Primary Examiner*—Lucille M. Phynes
*Attorney, Agent, or Firm*—Connolly and Hutz

[57] ABSTRACT

Hair-treatment agents having a content of branched copolyesters dispersible or soluble in water and an apparent molecular weight of 600 to 5000, and having a content of $SO_3M$ groups, wherein M represents an alkali metal ion or ammonium ion or the cationic radical of an organic amine.

23 Claims, 2 Drawing Figures

HAIR-TREATING AGENTS FROM BRANCHED, SULFO-GROUP CONTAINING COPOLYESTERS

Generally, hair-treatment agents, such as, for example, hair setting lotions, are used to set hair, to improve its texture and to give it shape. These shape-setting agents consist predominantly of a solution of resins or synthetic resins.

The preparations hiterto used thus contain, for example, the following resins or synthetic polymers alone or in combination: shellac, polyvinylpyrrolidone, polyvinylpyrrolidone copolymers, polymethacrylic acid esters, olefin-maleic acid anhydride copolymers, polysiloxanes, cellulose and derivatives, dimethyl-hydantoin-formaldehyde, polyacrylamides or polyvinyl acetate. Of these, polyvinylpyrrolidone and copolymers of vinylpyrrolidone and vinylacetate have so far proved to be the best. The solutions of these polymers, when applied, encase the treated hair with a more or less fixed coating of film which, depending upon the type of polymer used, may have a setting action, improve the texture of the hair, give the hair shape, improve the shine, make the hair sleek or have an anti-static action. The films formed on the hair should on the one hand be resistant to moisture, that is to say, the hair should not stick together even when atmospheric humidity is relatively high and should not loose shape, and on the other hand, when the hair is washed, it should be possible for these films to be washed out easily using an aqueous surfactant solution.

The hitherto known polymer film-formers such as, for example, polyvinylpyrrolidones, usually have the disadvantage of high water absorption at elevated atmospheric humidity, which, inter alia, results in the hair sticking together in an undesired manner and in a loss of firmness with consequent collapse of the hair style. If, on the other hand, the resistance to high humidity is improved such as, for example, with copolymers of vinylpyrrolidone and vinylacetate, the elasticity of the film suffers and the brittleness of the film can result, after the hair treatment, in an unpleasant dust and a flakey covering. Furthermore, it is very difficult to wash the preparation out of the hair. Also the customary commercial polymers often have a disadvantageous smell which is generally caused by the traces of monomer which cannot be completely avoided in the commercial production of these polymers.

Surprisingly, it has now been found that branched copolyesters dispersible or soluble in water, having an apparent molecular weight of between approximately 600 and approximately 5000 and a content of $SO_3M$ groups are ideally suited to the production of film-forming hair-treatment agents. It is possible to exceed or fall short of the limits given, but the intended effects of the hair-treatment agents according to the invention are not optimally achieved.

When used in practice, hair-treatment agents based on these branched sulfo group-containing polyesters have in particular the advantages listed hereinafter; products particularly successful in hair cosmetics for the intended purpose, such as polyvinyl-pyrrolidone, copolymers or vinylpyrrolidone and vinylacetate as well as shellac, have been used in the comparison experiments.

1. The hair-treatment agents according to the invention have a very low water absorption especially at high atmospheric humidity.

To improve this, 5 ml of a 5% aqueous solution of the particular polymer being examined, in a Petri dish having a diameter of 10 cm, was dried at 40° C. in a heating chamber until the weight was constant. The absorbing power was then examined at 25°C. and 65% as well as 95% relative atmospheric humidity after storing for 4 hours, in a closed climatic chamber, by determining the increase in weight of the polymer film. 10 measurements were taken in both conditions for each product and the mean value determined.

The water absorption of the film produced with the agent according to the invention was 5% (65% atmospheric humidity) and 29.5% (95% atmospheric humidity), see Table 1. The main effect of the low water absorption is that the style is not changed even at very humid times of the day and year and the hair does not stick together. Furthermore, the hair can also be better styled at the high atmospheric humidities that often exist in practice. The most important advantage of this low water absorption, however, is the shape stability of the hair style treated with the hair-treatment agent according to the invention.

TABLE 1

| Product | Water absorption (%) at 25° C. | |
|---|---|---|
| | 65% relative atmospheric humidity | 95% atmospheric humidity |
| Polyvinylpyrrolidone, mean molecular weight 40000 | 13.7 | 64.7 |
| Vinylpyrrolidone-vinyl-acetate copolymer in the ratio of 60:40 | 7.0 | 52.9 |
| Branched sulfo group-containing polyester[+] | 5.3 | 29.5 |

[+] obtained from
75 mole % of isophthalic acid
10 mole % of pyromellitic anhydride
15 mole % of 5-sodiumsulfonatoisophthalic acid dimethyl ester
100 mole % of diethylene glycol apparent molecular weight 700 to 1000.

2. A further advantage is the ease with which the branched sulfo group-containing polyester films can be washed out of the hair.

In analogy to the application of hair setting lotions in practice, 10 ml of a 3% aqueous solution of the compound used in accordance with the invention was applied to one half of the hair, parted in the middle of the head, of test persons, and the same quantity of a correspondingly concentrated solution of a comparative substance was applied to the other half. To ensure uniform distribution, the hair was combed through and the entire head of hair was pre-washed with 3 ml of an aqueous 10% solution of the sodium salt of lauryldiglycol ether sulfate and subsequently washed with 5 ml of the same surfactant solution analogously to normal practice. The hair was then rinsed with 2 litres of tap water of 20° dH and 32° C. The hair was then dried for 25 minutes with a commercial hood drier and combed out. Both halves of hair differed considerably in feel and softness depending on the quantity of polymer residue not washed out. It was shown that the branched polyester films produced on the hair with the agent according to the invention were washed out and left practically no residue, whereas other films, for example, shellac films, remained for the most part on the hair.

3. When the hair-treatment agents according to the invention are applied to the hair, contrary to most commercial agents, no sticking together of the still moist hair is observed (see Table 2). This adhesion of the hair treatment agent to the finger tips of the user of hairdresser when used, often observed with customary commercial polymers, is generally considered to be very unpleasant.

Examination of stickiness was carried out on the living hair of test persons. The head of hair was parted in the middle, moistened with 80 ml of distilled water and each half was treated with 10 ml in each case of a 3% aqueous solution of the substance to be examined. After combing through the moist hair the stickiness of the two hair areas was compared.

TABLE 2

| Product | Stickiness on moist hair |
| --- | --- |
| Polyvinylpyrrolidone, mean molecular weight 40000 | Very sticky |
| Vinylpyrrolidone-vinyl-acetate copolymer in the ratio of 60:40 | Slightly sticky |
| Branched sulfo group-containing polyester(+) | Not sticky |

(+) See Table 1

The hair-treatment agent with the branched polyester used in accordance with the invention did not exhibit any stickiness either when applied or after drying.

4. A further advantage of the hair-treatment agent according to the invention is the low number of dust particles after application to the hair. When customary commercial polymers are used, after applying them and drying the hair a troublesome covering is often apparent which is not very strongly fixed and causes deposits on the rims of hats, on clothing and on pillows etc. The dust particles are examined using a black comb by combing through hair strands prepared with the hair-treatment agents (3% aqueous solutions) 10 times. After combing the dried hair the comb was examined for visible residues. The results are given in Table 3.

TABLE 3

| Product | Residue on the comb |
| --- | --- |
| Shellac | Grey covering |
| Polyvinylpyrollidone, mean molecular weight 40000 | Some grey covering |
| Vinylpyrrolidone-vinyl-acetate copolymer in the ratio of 60:40 | Some grey covering |
| Branched sulfo group-containing polyester(+) | No visible residue |

(+)See Table 1

The hair treatment agents based on the branched polyesters used in accordance with the invention showed no residue on the comb.

5. A further advantage of the hair-treatment agents according to the invention is their high efficiency. The curl-retention test was used for comparison experiments. The test was carried out as follows.

1.5 grams of natural European hair was bunched together and cut to a length of 15 cm. The width was 2 cm. The strands were then washed in hand-warm water with the addition of an anionic surfactant (the sodium salt of alkyl ether sulfate) and rinsed out with warm water. The bunches of hair were then wound onto a hair curler of 2 cm diameter and dried for 30 minutes at 50° C. The curler was then removed, the hair combed through 3 times, put back into a curl and suspended for 2 hours at 65% relative atmospheric humidity and 20° C. The length of the curl was at first measured at 5 minute intervals and later at 15 minute intervals.

The base value L of the untreated curl was calculated by the mean value from 20 hair strands each of one gram.

In accordance with the same process the strands of hair were then treated with the hair-treatment agents to be examined, a 3% strength polymer solution being applied in a quantity of 0.4 ml/strand. 20 hair strands per measurement were used for each of the products examined. The test, carried out at 65% relative atmospheric humidity, was supplemented by further measurements at 95% relative atmospheric humidity and 20° C. likewise over a measuring time of 2 hours.

The percentage curl-retention was calculated in accordance with the following formula:

$$\% \text{ Curl-Retention} = \frac{L - L_t}{L - L_o} \cdot 100$$

$L$ = length of bunch of hair when extended (base value)
$L_o$ = length of curl at the beginning of the test
$L_t$ = length of curl after t minutes.

Figure 1:
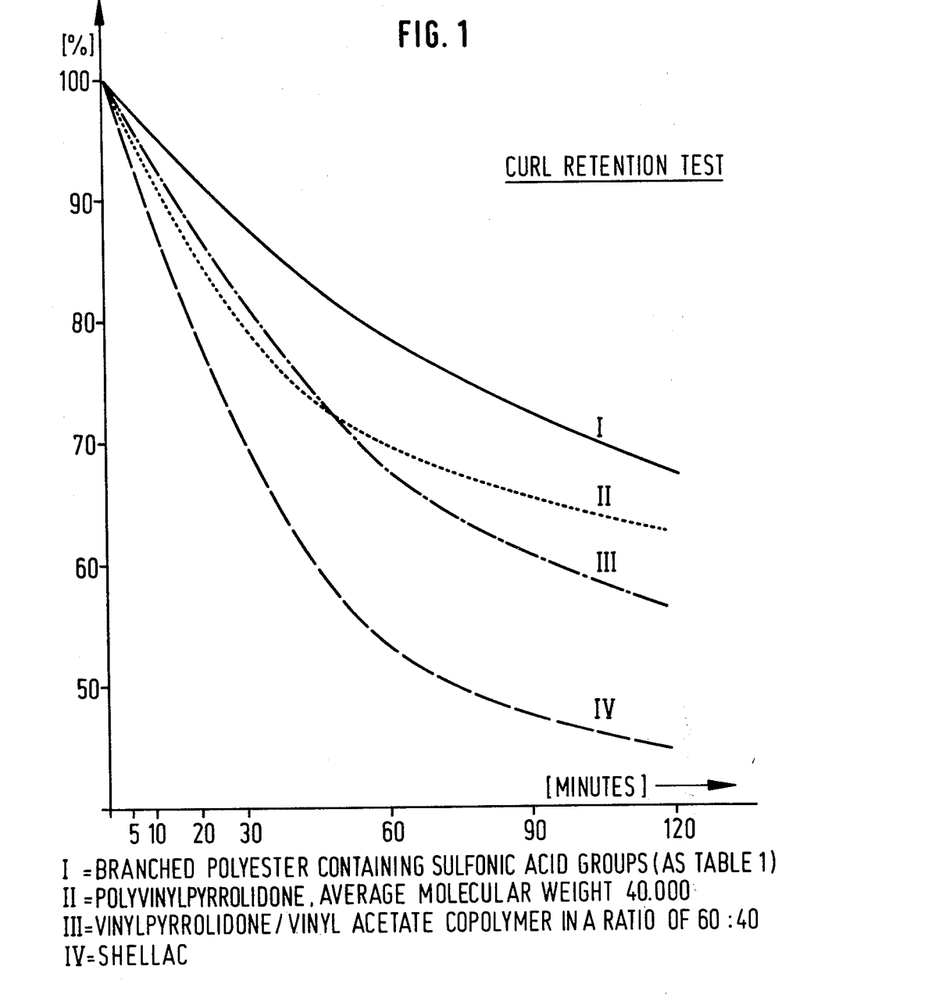
Figure 2:
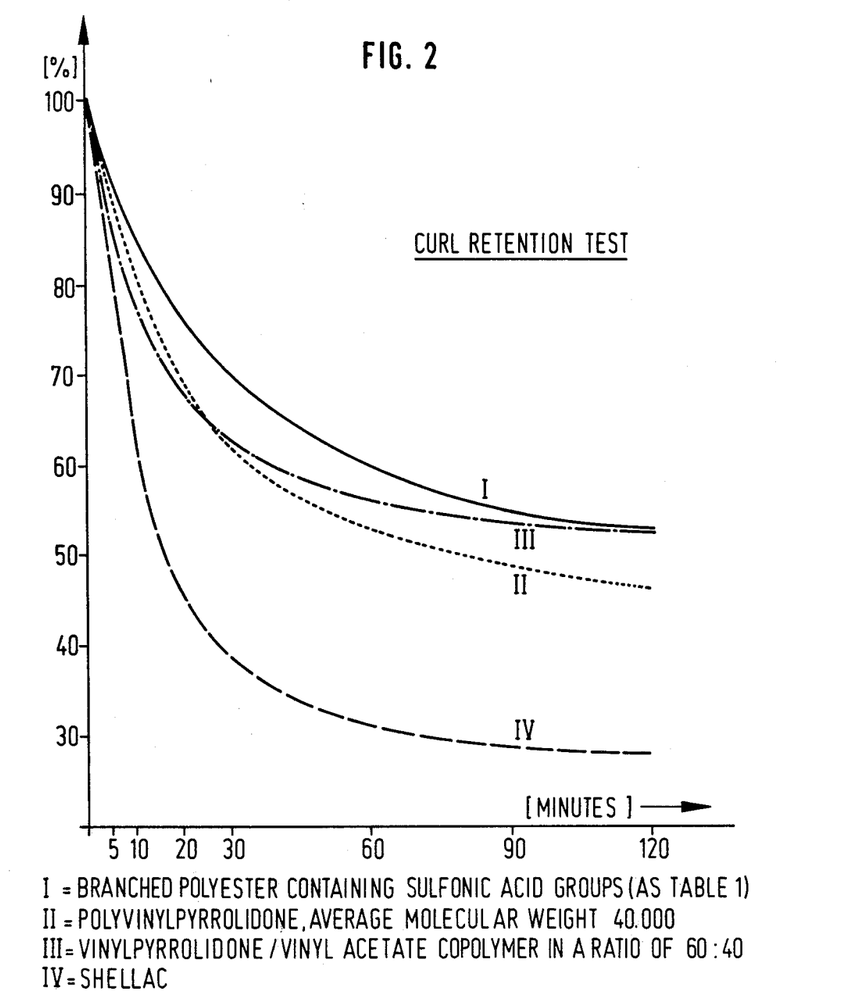

The results of the test at 65% relative atmospheric humidity are given in FIG. 1, and the values at 95% relative atmospheric humidity in FIG. 2, 3% strength solutions having been used in each case.

As may be seen from the graphs, when the hair-treatment agents according to the invention are used a much lower quantity of polymer is necessary to obtain a particular curl retention compared with the customary commercial preparations, thereby showing that the product is especially efficient.

6. Hair treatment agents that contain polyester branched in accordance with the invention produce a particularly smooth, transparent and shiny film on the hair. Good anti-friction properties are obtained which are chiefly noticeable in the ease with which dry or moist hair can be combed.

To judge the anti-friction properties comparison experiments as described under 3 were carried out. The especial ease with which the half of hair treated with the agent according to the invention can be combed when wet was observed by combing the hair when still moist; its combability when dry also assessed to be very good. The hair treated with the hair treatment agent according to the invention subsequently neither stuck together nor matted.

7. The hair-treatment agents produced in accordance with the invention with the branched polyesters are practically odorless, which is of great advantage for their use as a raw material in cosmetics. A large number of polymers on the market do not have this property. They frequently have an unpleasant smell, which is difficult to remove, especially as a result of a small content of monomer or residues of the starting material.

8. The hair-treatment agents according to the invention are especially characterised by their vaery positive influence on the hold of the hair style. This is attributable, inter alia, to the good elasticity of the film and is of great importance when used in hair-treatment agents. Examination of the hold is carried out by the curl retention test in point 5. The results are given in Table 4.

TABLE 4

| Product in 3% strength solution in each case | Curl retention test at 65% relative atmospheric humidity after 1 hour |
| --- | --- |
| Shellac | 53.3% |

TABLE 4-continued

| Product in 3% strength solution in each case | Curl retention test at 65% relative atmospheric humidity after 1 hour |
|---|---|
| Polyvinylpyrrolidone, mean molecular weight 40000 | 70.2% |
| Vinylpyrrolidone-vinyl-acetate copolymer in the ratio of 60:40 | 67.6% |
| Branched sulfo group-containing polyester (see Table 1) | 78.8% |

The obtained value of 78.8% is high compared with the customary commercial polymers examined and therefore, in practice, results in a better curl durability and hold of the hair style.

The copolyester used in accordance with the invention has an apparent molecular weight of approximately 600 to 5000, especially 700 to 4000, and contains $SO_3M$ groups, in which M represents an alkali metal ion, especially a sodium ion, an ammonium ion or the cationic radical of an organic amine, such as, especially, trimethylamine, triethylamine or triethanolamine. The polyester used in accordance with the invention preferably contains 5 to 40 mole %, especially 10 to 30 mole % of $SO_3M$ groups, calculated on the dicarboxylic and/or polycarboxylic acids used for the preparation of the polyester.

The polyester used in accordance with the invention is made up to the following radicals (A)

(A₁)

(B)

(B₁)

in which
  R₁ is a single bond or a divalent aliphatic, cycloaliphatic or aromatic radical, which may also contain an $SO_3M$ group,
  m represents the number 0, 1 or 2,
  R₁' represents an aliphatic, cycloaliphatic or aromatic radical which may also carry an $SO_3M$ group, and which when m = 0 is trivalent, when m = 1 is tetravalent and when m = 2 is pentavalent,
  R₂ represent a divalent aliphatic, cycloaliphatic or araliphatic radical which may also contain an $SO_3M$ group,
  n represents the number 0, 1 or 2,
  R₂' represents an aliphatic or cycloaliphatic radical which when n = 0 is trivalent, when n = 1 is tetravalent and when n = 2 is pentavalent may also contain a $SO_3M$ group.

The polyester used in accordance with the invention is branched by way of the radicals A₁ and/or B₁. Polyesters with only 1 branch or 2 branches in the radicals A₁ and/or B₁ are normally preferred, that is m and/or n preferably stand for 0 or 1.

In the polyester used in accordance with the invention, generally 80 to 140 mole % of radicals (B + B₁) and 1 to 40 mole %, preferably 5 to 40 mole % of branching radicals (A₁ + B₁) are present calculated on 100 mole % of the radicals (A + A₁).

It is advantageous if at least 40 mole % of the radicals A consist of radicals of the formula (A₂)

which may also contain an $SO_3M$ group.

Preferably, at least 40 mole % of the radicals A consist of the radicals of the formula (A₃)

which may also contain an $SO_3M$ group.

It is furthermore advantageous if at least 40 mole % of the radicals (B+B₁) are present in the form of radicals of the formula

—O—CH₂CH₂OCH₂CH₂O— and/or

—O—CH₂CH₂OCH₂CH₂OCH₂CH₂O—.

An equivalent portion of the radicals A and B can be replaced by radicals of the formula (C)

—O—R₃—C— in which R₃ represents a divalent, aliphatic, cycloaliphatic, or araliphatic radical, which may also contain an $SO_3M$ group.

An equivalent portion of the radicals A₁ and B₁ can be replaced by radicals of the formula

(C₁)

in which p and q represent 0, 1, 2 or 3 and p and q are so selected that (q+p)=1, 2, or 3 and R₃' represents an aliphatic radical.

R₃' therefore represents a trivalent aliphatic radical when (q+p)=1, a tetravalent aliphatic radical when (q+p)=2 and a pentavalent aliphatic radical when (q+p)=3. Consequently 1, 2 or 3 branches are incorporated into the polyester by the radical C₁. C₁ radicals with 1 or 2 branches, in which, therefore, (q+p)=1 or 2, are preferred.

The copolyesters according to the invention may be produced in a manner known per se by the condensation of dicarboxylic acids of the formula (A')

with diols of the formula

HO—R$_2$—OH  (B')

wherein a component having a branching action (A$_1'$)

and/or (B$_1'$)

must be present during the condensation and at least one component must possess an SO$_3$N group. It is possible to use, instead of the carboxylic acids, their esters, especially those with readily volatile lower alcohols having 1 to 4 carbon atoms, or their anhydrides or acid halides. Condensation is, as usual, carried out at an elevated temperature of 100° to 280° C., especially 150° to 230° C., preferably in an inert gas atmosphere, such as, for example, under nitrogen or carbon dioxide, the volatile condensation products (water and/or alcohols) as well as, where applicable, excess starting components usually a diol, being distilled off. It may be advantageous towards the end of the condensation to apply a vacuum of, for example, 10 to 15 torr or if desired lower (0.5 torr.) in order substantially to remove the volatile products. The condensation normally lasts for 3 to 15 hours and is carried out until the desired molecular weight is obtained. Care must always be taken that crosslinking of the copolyester does not occur as a result of the condensation process having gone too far because otherwise the products are not water-soluble and are unsuitable for the purpose of the invention.

For the condensation process, all of the components to be used can therefore be subjected to the polycondensation reaction from the beginning, that is introduced at the start. They may also, however, be added in stages in any order, so that the portions added first may form precondensates. In particular, components having a branching action are advantageously not added until later. Components having a pronounced branching action, such as, for example, pentaerythritol, are advantageously not added until relatively late in the reaction.

The polycondensation reaction can be carried out either with the customary esterification or transesterification catalysts (alkali alcoholates, titanium alcoholates, manganese acetate, zinc acetate etc.) or completely without such catalysts. Both of these may have their special advantages and when the reaction carried out is in other respects the same, depending upon which procedure is followed different products are obtained, particularly, of course, regarding the molecular weight and the solubility.

For example, it is possible to use as transesterification catalysts alkali metal hydroxides, such as sodium or potassium hydroxide, or alkali metal alcoholates such as sodium methylate or ethylate, alkaline earth oxides or hydroxides, such as, for example, the appropriate calcium or magnesium compounds, as well as zinc or cadmium oxide, salts of organic carboxylic acids, such as sodium, calcium or zinc acetate or formate, organic titanium compounds, especially titanium alcoholates, such as, for example, titanium isopropylate or titanium butylate inter alia. The quantities used depend chiefly upon the activity of the particular catalyst. The quantity of catalyst is normally kept as low as possible.

In the preparation of the copolyesters used in accordance with the invention, a portion of the components (A'+B') can be replaced by an equivalent portion of one or more hydroxycarboxylic acids of the formula (C')

A portion of the branching components (A$_1'$+B$_1'$) can be replaced by an equivalent portion of one or more branching components of the formula C$_1'$

(C$_1'$)

In this formula R$_3$, R$_3'$, q and p have the meanings already given.

The apparent mean molecular weight is determined in a vapor pressure osmometer using dimethylformamide as solvent. On account of the dissociation of the sulfonate groups the actual mean value of the molecular weight is higher than the apparent value measured in this manner. The value measured is, however, a sufficiently accurate criterion for characterising the degree of condensation of the mixed polyesters according to the invention and for determining the end of the condensation reaction.

If, when carrying out the copolycondensation reaction, components of which at least one possesses an SO$_3$M group are used then copolyesters that can be used in accordance with the invention are obtained directly. They may however, alternatively be obtained by subsequently introducing SO$_3$M groups into a branched and unsaturated polyester by reacting with bisulfite. To do this, first of all a branched and unsaturated polyester is produced, wherein components free of SO$_3$M are used and the components are so selected that at least one of them contains one or more unsaturated aliphatic carbon-carbon bonds. Normally, 5 to 40 mole % of such a component, preferably 10 to 30 mole % of such a component, calculated on the polycarboxylic component consisting of the compounds (A'+A$_1'$), are used and the other components are selected as indicated above. Suitable compounds having unsaturated C—C bonds are, especially, maleic acid, fumaric acid and itaconic acid as well as their lower esters and anhydrides. A quantity of MHSO$_3$ solution, especially an NaHSO₃ solution, equivalent to the unsaturated C—C bonds present in the polyester is then added to the branched and unsaturated polyester so produced, at an elevated temperature of approximately 50° to 100° C., preferably 90° to 100° C. As a result of the following addition of MHSO₃ to the unsaturated C—C bonds copolyesters that can be used in accordance with the invention are obtained. The dicarboxylic acid components that come into consideration for the production of the copolyestes are chiefly any dicarboxylic acids A':

(A')

that can be used for preparing polyesters, or their corresponding acid halides, anhydrides or esters which produce in the finished polyester the radical

(A)

in which $R_1$ represents a single bond or a divalent aliphatic, cycloaliphatic or aromatic radical and this radical may also carry an $SO_3M$ group. Preferably $R_1$ represents a divalent aliphatic radical having 2 to 8 carbon atoms, a divalent cycloaliphatic radical having 6 to 8 carbon atoms or a divalent aromatic radical having 6 to 12 carbon atoms. Examples of suitable aliphatic, cycloaliphatic and aromatic dicarboxylic acids are: oxalic acid, malonic acid, succinic acid, methylmalonic acid, glutaric acid, dimethylmalonic acid, adipic acid, pimelic acid, suberic acid, 2,2-dimethylglutaric acid, azelaic acid, trimethyladipic acid, sebacic acid, fumaric acid, maleic acid, itaconic acid, 1,2-cyclohexanedicarboxylic acid, 1,3-cyclohexanedicarboxylic acid, 1,4-cyclohexanedicarboxylic acid, norbornanedicarboxylic acid, phthalic acid, isophthalic acid, terephthalic acid, 1,4-naphthalenedicarboxylic acid, 2,5-naphthalenedicarboxylic acid and diphenic acid. The carbon skeleton of the dicarboxylic acids that come into consideration may also be interrupted by hetero atoms, such as oxygen or sulfur, or hetero groups, such as —SO₂—. Examples of these are diglycolic acid, thiodipropionic acid, 4,4'-oxydibenzoic acid or 4,4'-sulfonyldibenzoic acid.

The dicarboxylic acids listed may, as already mentioned, alternatively be used in the form of their esters, anhydrides or acid halides. The acid halides preferred are acid chlorides. The esters that come into consideration are those with readily distillable monoalcohols, that is preferably those having 1 to 4 carbon atoms. On the other hand, however, esters with diols, dealt with hereinafter, also come into consideration. Suitable esters, anhydrides and acid chlorides for the component A', or for incorporating A, are, for example:

terephthalic acid dimethyl ester
terephthalic acid diethyl ester
terephthalic acid dipropyl ester
terephthalic acid diisopropyl ester
terephthalic acid dibutyl ester
isophthalic acid dimethyl ester
isophthalic acid diethylester
isophthalic acid dipropyl ester
isophthalic acid dibutyl ester
isophthalic acid diisobutyl ester
phthalic acid dimethyl ester
phthalic acid diethyl ester
phthalic acid dipropyl ester
phthalic acid diisopropyl ester
phthalic acid dibutyl ester
malonic acid dimethyl, diethyl, dipropyl or dibutyl ester,
succinic acid dimethyl or dibutyl ester,
glutaric acid diethyl or diisopropyl ester,
adipic acid diethyl or diisobutyl ester,
pimelic acid dimethyl, diisopropyl or dibutyl ester,
suberic acid dimethyl, diethyl, dipropyl or dibutyl ester,
1,4-cyclohexanedicarboxylic acid dimethyl, diethyl, dipropyl or dibutyl ester,
1,2-cyclohexanedicarboxylic acid dimethyl, diethyl, dipropyl or dibutyl ester,
1,3-cyclohexanedicarboxylic acid dimethyl, diethyl, dipropyl or dibutyl ester,
phthalic acid anhydride
maleic acid anhydride
succinic acid anhydride
phthalyl chloride.

The copolyester that can be used in accordance with the invention contains, calculated on the radicals $A_1$ present, preferably at least 40 mole % of radicals of the formula (A₂)

that is, it is advantageous when preparing the copolyester to use at least 40 mole %, calculated on the component A', of a benzenedicarboxylic acid of the formula (A₂')

that is phthalic acid, isophthalic acid or terephthalic acid or their esters, their anhydrides where existent, or their acid chlorides. Particularly good results are obtained if at least 40 mole %, calculated on the component A', of radicals of the formula

(A₃)

are incorporated in the copolyester. It is therefore particularly advantageous to use in the preparation of the copolyester at least 40 mole %, calculated on the component A', of isophthalic acid of the formula

(A₃')

or an ester thereof, especially isophthalic acid dimethyl ester or mixtures of 2 or 3 benzenedicarboxylic acids which predominantly contain isophthalic acid or the esters thereof.

The diol components that come into consideration for the production of the copolyesters to be used in accordance with the invention are chiefly any diols B':

HO—R$_2$—OH          (B')

that can be used to produce polyesters and incorporate in the finished polyester the radical —O—R$_2$—O—          (B)

in which R$_2$ represents a divalent aliphatic, cycloaliphatic or araliphatic radical which may also carry an SO$_3$M group.

In particular, R$_2$ represents a divalent aliphatic radical having 2 to 10 carbon atoms, especially such a radical with ether bridges. The indicated preferred range of 2 to 10 carbon atoms for the latter relates, however, only to the part between 2 ether bridges or oxygen atoms. The divalent aliphatic radical of ether bridges may have a molecular weight of up to 2000.

Furthermore, R$_2$ represents in particular a divalent radical of a polyethylene glycol of a molecular weight of 300 to 2000 or an ethylene-propylene-polyglycol of a molecular weight of 300 to 2000. In particular, R$_2$ also represents a divalent cycloaliphatic radical having 6 to 10 carbon atoms or a divalent araliphatic radical having 8 to 14 carbon atoms.

Examples of suitable diols B' yielding the radical B are:

ethylene glycol,
1,2-propanediol and 1,3-propanediol,
butanediol, especially
1,4-butanediol,
butanediol, such as 1,5-pentadiol,
hexanediols, especially
1,6-hexanediol
1,10-decanediol
diethylene glycol
dipropylene glycol
triethylene glycol
tetraethylene glycol
tripropylene glycol
polyethylene glycol having a molecular weight of 300–2000
bis-(4-hydroxybutyl)-ether
2-methylenepropane-1,3-diol,
2,4-dimethyl-2-ethylhexane-1,3-diol,
2-ethyl-2-butyl-propane-1,3-diol,
2,2-dimethylpropane-1,3-diol,
2-ethyl-2-isobutylpropane-1,3-diol,
2,2,4-trimethylhexane-1,6-diol,
1,3-dihydroxycyclohexane,
1,4-dihydroxycyclohexane (quinite)
1,4-bis-(hydroxymethyl)-cyclohexane
1,3-bis-(hydroxymethyl)-cyclohexane
1,2-bis-(hydroxymethyl)-cyclohexane
1,4-bis-(hydroxymethyl)-benzene
1,3-bis-(hydroxymethyl)-benzene
2,6-bis-(hydroxymethyl)-naphthalene

Furthermore, suitable components B' are, for example, diphenols which have been converted into araliphatic bishydroxy compounds by reacting at both ends with ethylene oxide and with which, for example, the general formula B$_2$'

(B$_2$')

in which
r = 0 or 1
s = 1, 2, 3 or 4 may be associated. The compounds of the formula B$_2$' may also carry SO$_3$M groups. By means of these compounds, the radical B$_2$ (B$_2$)

in which r and s have the meanings mentioned, is incorporated in the copolyester molecule. In the calculation of the mole percentages, B$_2$ is classed with the radicals B, and B$_2$' with the components B'; examples of suitable components of B$_2$' are as well as other products multiply oxethylated at both ends.

Instead of the dicarboxylic acids A' and diols B', it is possible to use hydroxycarboxylic acids C' or their esters, which incorporate in the finished copolyester the radical

(C)

in which R$_3$ represents a divalent aliphatic, cycloaliphatic or araliphatic radical which may also contain an SO$_3$M group. In particular, R$_3$ represents a divalent aliphatic radical having 1 to 10 carbon atoms, a divalent cycloaliphatic radical having 6 to 11 carbon atoms, a divalent araliphatic radical having 8 to 12 carbon atoms, wherein, in the araliphatic radical the aliphatic part may be separated from the aromatic part by a hetero atom or the aliphatic part may be interrupted by a hetero atom. The hetero atom that comes into consideration in particular is oxygen. Examples of suitable hydroxycarboxylic acids C' delivering the radical C are:

glycolic acid
lactic acid
3-hydroxypropionic acid
4-hydroxybutyric acid
5-hydroxy-3-pentenic acid mandelic acid
3-hydroxymethylcyclohexanecarboxylic acid
4-hydroxymethylcyclohexanecarboxylic acid
6-hydroxymethyl-decalin-2-carboxylic acid

Examples of suitable esters of hydroxycarboxylic acids C' are:
lactic acid methyl ester
lactic acid ethyl ester
4-hydroxybutyric acid methyl ester mandelic acid ethyl ester

As already mentioned, the radicals standing for $R_1$, $R_2$, $R_3$, $R_1'$, $R_2'$, and $R_3'$ may also contain an $SO_3M$ group. Also the radicals $A_2$, $A_3$ and $B_2$ may contain an $SO_3M$ group. Aliphatic, cycloaliphatic, aromatic or araliphatic compounds may be used as compounds A', B' and C' containing $SO_3M$ groups.

Suitable compounds A', $A_2'$ and $A_3'$ carrying $SO_3M$ groups, and their esters, anhydrides or acid chlorides are, for example:

sodium sulfosuccinic acid
potassium sulfosuccinic acid
ammonium sulfosuccinic acid
4-sodium sulfophthalic acid
4-sodium sulfophthalic acid anhydride
4-potassium sulfophthalic acid
2-sodium sulfoterephthalic acid
2-sodium sulfoterephthalic acid dichloride
5-sodium sulfoisophthalic acid
5-sodium sulfopropoxyisophthalic acid
5-sodium sulfoethoxyisophthalic acid sodium sulfosuccinic acid dimethyl ester
sodium sulfosuccinic acid diethyl ester
4-sodium sulfophthalic acid diethyl ester
4-sodium sulfophthalic acid dimethyl ester
4-ammonium sulfophthalic acid dimethyl ester
2-sodium sulfoterephthalic acid diethyl ester
5-sodium sulfoisophthalic acid dimethyl ester
5-sodium sulfopropoxyisophthalic acid dimethyl ester
5-sodium sulfoethoxyisophthalic acid diethyl ester
5-sodium sulfoethoxyisophthalic acid diisopropyl ester
5-potassium sulfoethoxyisophthalic acid di-n-propyl ester

Examples of hydroxycarboxylic acids C' carrying $SO_3M$ groups, and the esters thereof are:

Examples of compounds B' carrying $SO_3M$ groups are:

-continued

It may be seen from the Examples that the SO₃M group may be bonded to the actual carbon skeleton of the molecule of the compounds A', $A_1'$, $A_2'$, $A_3'$, C', $C_1'$ and B' either directly or indirectly, for example by means of radicals such as —OCH₂CH₂, —O—CH₂CH₂CH₂— or The copolyester used in accordance with the invention are branched. To produce the copolyesters it is therefore necessary to use in addition to the components A' and B' already mentioned, as well as, where applicable, $A_2'$, $A_3'$ and/or C', components by means of which a branch is incorporated in the copolyester.

Such branching components may be:

a. The polycarboxylic acids, $A_1'$ with 3, 4, or 5, preferably 3 carboxyl groups, or their esters, especially with lower alcohols having 1 to 4 carbon atoms, their anhydrides or acid chlorides.

b. The polyhydroxy compounds $B_1'$ with 3, 4 or 5, preferably 3 hydroxyl groups.

c. The hydroxycarboxylic acids $C_1'$ with up to a further 3 hydroxyl or carboxylic acid groups.

Also, the polycarboxylic acids $A_1'$ with 3, 4 or 5, preferably 3 or 4 carboxyl groups, mentioned above under (a) may, if desired, carry an SO₃M group. Compounds of the formula $A_1'$ introduce the radical $A_1$ into the copolyester molecule, the number of branches $Z_A$ that are incorporated in the copolyester molecule by a radical $A_1$ or a compound $A_1'$ being $Z_A = m + 1$.

If the radical $R_1'$ contained in $A_1$ is an aliphatic radical, then it may contain especially 2 to 5, preferably 2 to 3 carbon atoms; if it represents a cycloaliphatic radical, then those having 6 to 8, preferably 6 carbon atoms come into consideration, and if it is an aromatic radical, especially those having 6 to 12, preferably 6 to 10 carbon atoms come into consideration.

Suitable compounds $A_1'$ which incorporate the group $A_1$ in the copolyester molecule are, for example;

trimellitic acid
trimesic acid
hemimellitic acid
mellophanic acid
prehnitic acid
pyromellitic acid
aconitic acid
tricarballyl acid
ethanetetracarboxylic acid Anhydrides are also suitable, such as, for example;

trimellitic acid anhydride
pyromellitic acid anhydride
hemimellitic acid anhydride
mellophanic acid dianhydride
prehnitic acid anhydride Esters, especially with alchohols having 1 to 4 carbon atoms, are also suitable, such as, for example;

trimellitic acid trimethyl ester
trimellitic acid triethyl ester
trimesic acid trimethyl ester
hemimellitic acid trimethyl ester
mellophanic acid tetramethyl ester
prehnitic acid tetramethyl ester
pyromellitic acid tetramethyl ester
pyromellitic acid tetraethyl ester Also suitable are, for example:

1,2,3-cyclohexanetricarboxylic acid
1,2,4-cyclohexanetricarboxylic acid
1,2,5-cyclohexanetricarboxylic acid naphthalenetricarboxylic acid Also, the polyhydroxy compounds $B_1'$ with 3, 4 or 5, preferably with 3 or 4 hydroxyl groups, mentioned above under (b), may, if desired, contain an SO₃M group. The number of branches $Z_B$ that are incorporated in the copolyester molecule by a radical $B_1$ or a compound $B_1'$ is: $Z_B = n + 1$.

If the radical $R_2'$ in $B_1'$ represents an aliphatic radical, it may contain especially 3 to 12, preferably 3 to 6 carbon atoms, and if it is cycloaliphatic radical it may contain especially 6 to 8 and preferably 6 carbon atoms.

Suitable compounds $B_1'$ are, for example:

glycerin
erythritol
pentaerythritol
trimethylolpropane
trimethylolethane

Especially suitable are those compounds $B_1'$ in which $n = 0$ or 1, and which accordingly contain three or four hydroxyl groups in the molecule. With these compounds there is less danger of overdosing when preparing the copolyester which would lead to crosslinking to form insoluble products.

Also, the hydroxycarboxylic acids $C_1'$ having up to 3 further hydroxyl or carboxylic acid groups mentioned under (c) may, if desired, contain an SO₃M group. The number of branches $Z_C$, that are incorporated in the copolyester molecule by a radical $C_1$ or a compound $C_1'$ is: $Z_C = q + p$.

If the radical $R_3'$ contained in $C_1'$ represents an aliphatic radical then it may contain especially 2 to 8, preferably 2 to 4 carbon atoms.

Suitable compounds $C_1'$ are, for example:

citric acid
malic acid
tartaric acid.

It is also possible to use instead of the free hydroxycarboxylic acids of the formula $C_1'$ corresponding derivatives, especially the corresponding esters with lower alcohols, that is with 1 to 4 carbon atoms, for example:

citric acid trimethyl ester,
malic acid dimethyl ester,
tartaric acid dimethyl ester.

As in the case of the compounds $B_1'$, if products that are not for special purposes are produced, also in the case of the compounds $A_1'$ and $C_1'$ those are normally preferred that incorporate only one or two branches in the copolyester molecule, that is in which $m=0$ or 1 and $q+p=1$ or 2, because the danger of overdosing with these leading to crosslinking is minimal.

80 to 140 mole % of the polyol component consisting of the compounds $B'$ and $B_1'$, calculated on 100 mole % of the polycarboxylic acid component consisting of the compounds $A'$ and $A_1'$, are normally used to prepare the copolyesters (compounds $B_2'$ present are classed with the compounds $B'$), and the components are so selected that, calculated on 100 mole % of the di- and-/or polycarboxylic acid component, 5 to 40 mole %, preferably 10 to 30 mole % of $SO_3M$ groups are present or, if the $SO_3M$ groups are introduced by adding to a prepared $SO_3M$-free copolyester, 5 to 40 mole %, preferably 10 to 30 mole % of unsaturated C—C bonds are present. Normally, 1 to 40 mole %, preferably 5 to 40 mole % of branching components ($A_1'+B_1'$) are used calculated on 100 mole % of polycarboxylic acid component ($A'+A_1'$). Advantageously at least 40 mole % of the compounds $A'$ consist of benzenedicarboxylic acids $A_2'$, especially of isophthalic acid $A_3'$. Furthermore, it is advantageous if the compounds of the polyol component consisting of the compounds $B'+B_1'$ are so selected that at least 40 mole % of diethylene glycol and/or triethylene glycol are used calculated on 100 mole % of ($B'+B_1'$).

If hydroxycarboxylic acids $C'$ or $C_1'$ are used in the preparation of the copolyester, these compounds must be allotted mathematically to the polycarboxylic acid and polyol component or to the branching component ($A_1'+B_1'$) in the calculation of the mole percentages in accordance with the number of hydroxyl and carboxyl groups. Thus, for example, in the calculation of the mole percentages, one half of the carboxylic acid of the general formula $C'$ is added to the component $A'$ and the other half to the component $B'$. Of the components $A'$, $A_1'$, $A_2'$, $A_3'$, $B'$, $B_1'$, $B_2'$, $C'$ and $C_1'$ in each case one representative or several representatives may be used for the preparation of the copolyesters. In the preparation of the copolyesters, the incorporation of the radicals A, $A_1$, $A_2$, $A_3$, B, $B_1$, $B_2$, C and $C_1$ is effected statistically. For this reason and because of the branches present it is not possible to give a simple formula for the copolyester used in accordance with the invention. Where the number of branches was indicated hereinbefore, for example, by 1, this means that 1 to 40 mole %, preferably 5 to 40 mole % of the radicals $A_1$ in which $m=0$ and/or $B_1$ in which $n=0$ and/or $C_1$ in which $(q+p)$ are statistically distributed, in the polyester according to the invention calculated on 100 mole % of the radicals ($A+A_1$).

The copolyesters used in accordance with the invention are truly or colloidally soluble in water, or are at least readily dispersible therein without the use of special dispersing agents or any other means. It is also possible to use the copolyesters in accordance with the invention in other solvents and may even be advantageous. An addition of other solvents, preferably of alcohols such as methanol or ethanol, or dipolar aprotic solvents, such as dimethylformamide or dimethylsulfoxide, has proved advantageous. They are distinguished by providing the solutions with a good storage stability.

The copolyesters used in accordance with the invention may be combined with solvents and additives customarily used in the preparation of hair-treatment agents. Thus they may be used, for example, in hairsetting lotions, hair lotions, hair rinsing agents, hair shampoos, hair coloring agents, hair tonics, hairdressing creams and other hair-treatment agents. These preparations may be present in liquid, semi-solid or solid form and applied to the hair in known manner, for example, by spraying on, pouring on, rubbing in or soaking in.

Suitable solvents and additives are, for example, water, mixtures of in particular low molecular weight alcohols, such as, for example, ethanol, propanol, isopropanol and water, cetyl alcohol, stearyl alcohol, methylene chloride, Vaseline, Vaseline oil, isopropyl myristate, palmitate and stearate, ethers, polyhydric alcohols, such as, for example, glycol, glycerin, sorbitol, polyglycols, natural fats and oils, silicone oils, wool wax alcohols, wool fat (anhydrous), oxethylated wool fat, butyl stearate, liquid paraffin, as well as emulsifiers, wetting agents, surfactants, suitable coloring and bleaching agents, thickeners, such as, for example cellulose ethers, scalp-care agents, for example, allantoin, perfumes, preservatives, plant extracts and agents for protection against the sun. Also, a combination with quatenary ammonium compounds to form electron neutral salts is possible.

The branched, sulfo group-containing polyesters used in accordance with the invention may also be combined with other polymers, such as, for example, shellac, polyvinylpyrrolidone, polyvinyl acetate, vinylpyrrolidone-vinyl acetate copolymers, polyvinylmethyl ethers, vinyl acetate-crotonic acid copolymers, carboxylated vinyl acetate terpolymers or alkyl esters of acrylic acid. The appropriate mixing ratio may vary widely depending on the intended effect in the field of application.

The quantitative proportion of sulfo group-containing polyesters used in accordance with the invention in the hair-treatment agents can vary, depending on the desired effect from approximately 0.1 to approximately 10% but preferably from 0.5 to 4%, calculated on the weight of the prepared formulation.

The preparation of the hair-treatment agents according to the invention, which depending on the composition, is concerned with, for example, solutions, dispersions, creams, oils or emulsions, is carried out in a manner known per se by mixing the components at room temperature or, in special cases, such as for example in the case of emulsions, optionally with the action of heat.

The following Examples are to illustrate the invention but in no way represent a limitation.

The following abbreviations are used in the Examples:

IPA = isophthalic acid
DMI = isophthalic acid dimethyl ester
DMT = terephthalic acid dimethyl ester
SIM = 5-sodimsulfonato-isophthalic acid dimethyl ester
K-SIM = 5-potassiumsulfonato-isophthalic acid dimethyl ester
SPO = 5-sodiumsulfonatopropoxy-isophthalic acid dimethyl ester
TPA = terephthalic acid
TMSA = trimellitic acid anhydride
MA = maleic acid anhydride
DEG = diethylene glycol
TEG = triethylene glycol
TMP = trimethylol propane

EXAMPLE 1

Liquid Hair-Setting Lotion 3 g of a polyester obtained from 75 mole % of isophthalic acid, 10 mole % of pyromellitic anhydride, 15 mole % of 5-sodiumsulfonatoisophthalic acid dimethyl ester and 100 mole % of diethylene glycol which has an apparent molecular weight of 700 to 1,000, are dissolved, while stirring gently, in 50 g of distilled water, and this solution is mixed with 46.8 g of isopropyl alcohol into which 0.2 g of perfume oil has been previously introduced. The polyester may be prepared as follows: 311 g of isophthalic acid, 111 g of 5-sodiumsulfonatoisophthalic acid dimethyl ester, 54.5 g of pyromellitic acid dianhydrode and 265 g of diethylene glycol are heated in a nitrogen atmosphere over a period of 1 hour to a temperature of 150° C. in a 4-necked flask provided with an agitator, a thermometer, a gas inlet pipe and a descending cooler, then the temperature is increased by 10° per hour until, after 6 hours, 210° C. is reached. The mixture is then heated for a further 2 hours under nitrogen at 210° to 215° C. and a reduced pressure of 10 to 12 mm/Hg is then applied for 10 minutes. 640 g of an amber colored residue are obtained which dissolves in pure water in a milky-colloidal manner with a pH value of approximately 2.2. The pH value of this solution is adjusted to 6.0 with approximately 85 ml of a sodium hydroxide solution of 25% strength, as a result of which the solution becomes water-clear. By diluting with water to 2,140 g the solution is adjusted to 30% strength. The apparent molecular weight is between 700 and 1,000.

EXAMPLE 2

Liquid Hair Setting Lotion 0.2 gram of diisopropyl adepate and 0.2 gram of perfume oil are mixed with 47.6 grams of ethyl alcohol. This mixture is stirred into a solution of 2 grams of the polyester mentioned in Example 1 in 50 grams of distilled water.

EXAMPLE 3

Liquid Hair-Setting Lotion with the Addition a Quaternary Ammonium Compound

First of all, a solution of 3 grams of the polyester mentioned in Example 1, 0.15 gram of pentaoxethylstearylammonium chloride and 50 grams of water is produced while stirring. A mixture of 0.1 gram of perfume oil and 46.75 grams of ethyl alcohol is then introduced into this solution.

EXAMPLE 4

Alcohol-Free Liquid Hair-Setting Lotion 0.1 gram of perfume oil is mixed with 0.2 gram of a perfume oil solubilizer (for example, the reaction product of 1 mole of castor oil and 40 moles of ethylene oxide) and made into a paste with 5 grams of water. This mixture is then stirred slowly with 92.7 grams of water in which 2 grams of the polyester mentioned in Example 1 have previously been dissolved.

EXAMPLE 5

Water in Oil-Hairdressing Cream with Setting Lotion 3 grams of trioleyl phosphate ((®) Hostaphat KO 300 N), 3 grams of monoglycol distearate, 2 grams of microcrystalline wax, 20 grams of paraffin oil and 6 grams of isopropyl stearate are heated together to a temperature of 70° to 75° C. Separately, a solution of 0.5 gram of the polyester mentioned in Example 1, 0.18 gram of p-hydroxybenzoic acid methyl ester, 0.02 gram of p-hydroxybenzoic acid propyl ester and 65.0 grams of water is heated to 85° C. This aqueous phase is then added in portions, while stirring, to the fat melt. The emulsion which forms is stirred until cold. At approximately 40° C., 0.3 gram of perfume oil is added. The cream can then be triturated on a cylinder mill.

EXAMPLE 6

Oil in Water—Hairdressing Cream with Setting Action 3 grams of trialkyltetraglycol ether-o-phosphate ((®) Hostaphat KW 340 N) 15 grams of paraffin oil and 2 grams of Vaseline are melted together at a temperature of 70° C. Separately, 0.18 gram of p-hydroxybenzoic acid methyl ester and 0.02 gram of p-hydroxybenzoic acid propyl ester are dissolved in 77.3 grams of hot water. After cooling to room temperature 0.5 gram of the polyester used in Example 1 and 0.8 gram of carboxyvinyl polymer ((®) Carbopol 934) are introduced while stirring and 0.9 gram of triethanol amine are added as a result of which a gel is formed. While stirring, this highly viscous aqueous phase is added to the fat-emulsifier melt, which is still hot. Subsequently, the mixture is stirred until cold and 0.3 gram of perfume oil is added when the emulsion is at a temperature of 40° C.

EXAMPLE 7

Hair-Rinsing Agent with Setting Action 5 grams of the reaction product of 1 mole of stearyl alcohol and 15 moles of ethylene oxide are melted with 3 grams of cetyl alcohol at a temperature of 70° C. Separately, 2 grams of alkyltrimethylammonium chloride and 0.5 grams of the polyester mentioned in Example 1 are heated to 75° C. in 89.3 grams of water. This aqueous phase is added in portions, while stirring, to the melt. The resulting emulsion is stirred until cold and at a temperature of 40° C. is scented with 0.2 gram of perfume oil.

EXAMPLE 8

Hair-Conditioning Cream with Setting Action 4 grams of the reaction product of 1 mole of stearyl alcohol and 15 moles of ethylene oxide, 6 grams of cetyl alcohol and 4 grams of paraffin oil are melted at 70° C. Separately, 1.5 grams of distearyl dimethylammonium chloride, 1 gram of plant extract and 0.5 gram of the polyester used in Example 1 are introduced into 82.8 grams of water and heated to 70° C. This aqueous mixture is added in portions, while stirring, to the melt. The resulting cream is stirred until cold and at a temperature of 40° C. is scented with 0.2 gram of perfume oil.

EXAMPLE 9

Hair Lotion with Setting Action 0.2 gram of perfume oil and 0.3 gram of diisopropyl adipate are dissolved in 30 grams of isopropyl alcohol and mixed with 69 grams of water, to which 0.5 gram of the polyester mentioned in Example 1 have previously been added.

EXAMPLE 10

Liquid Alcohol-Free Hair-Setting Concentrate 10 grams of the polyester mentioned in Example 1 are dissolved, while stirring, in 89.3 grams of water. A mixture of 0.2 gram of perfume oil and 0.5 gram of the reaction product of 1 mole of hydrogenated castor oil and 40 moles of ethylene oxide is then added to this solution and stirring is carried out.

It is possible to use other polymers, instead of the polyester used in the aforegoing Examples, a few of these and possible methods of preparation are listed in the following by way of example.

(I)

A product like that in Example 1 which can be used in a similar field of application is obtained by replacing the isophthalic acid in Example 1, completely or partially, by an equivalent amount of its dimethyl, diethyl, dipropyl or dibutyl ester. These products are less acidic the higher their proportion of ester.

Products of different elasticity are obtained by replacing a portion of the diethylene glycol in Example 1 by one or more other bis alcohols, for example, by b: 90 mole % of DEG; 10 mole % of polyethylene glycol 1000
c: 80 mole % of DEG; 20 mole % of polyethylene glycol 400
d: 70 mole % of DEG; 30 mole % of polyethylene glycol 300
e: 60 mole % of DEG; 10 mole % of dipropylene glycol; 10 mole % of monoethylene glycol; 20 mole % of PEG 600.

The hydrophilic property of the polycondensates increases with the increasing length of the polyglycol ether radical.

(II)

75 mole % of IPA; 10 mole % of TPA; 15 mole % of SPO; 80 mole % of DEG; 20 mole % of 1,6-hexanediol; 40 mole % of TMP 311 grams of isophthalic acid (degree of purity 99%), 41.5 grams of terephthalic acid, 133 grams of 5-sodium-sulfopropoxyisophthalic acid dimethyl ester, 212 grams of diethylene glycol, 59 grams of 1,6-hexanediol and 134 grams of trimethylol propane, without the addition of a catalyst, are heated over a period of one hour, under nitrogen, to 170° C., in a ground four-necked flask of 2 liter capacity equipped with agitator, thermometer, gas inlet pipe for nitrogen and descending cooler, then the tempterature in the flask is increased by a further 10° per hour over a period of 7 hours until 240° C. is reached. Finally, heating is carried out at 240°–245° C., while continuously stirring well, for a further 2 hours in a water jet vacuum of approximately 12 torr and for 1 hour in a medium-high vacuum of approximately 0.5 torr. Altogether approximately 170 grams of distillate (methanol, water and excess diol) were collected in the vessel. 705 grams of an amber-colored residue is obtained, which may easily be adjusted with water to 2350 grams to form a light, practically clear, 30% strength solution. The molecular weight is approximately 1420. The pH value of 4.3 is advantageously increased to 6.5 by stirring in very little strong sodium hydroxide solution.

If the heating time in vacuo at 240°–245° C. is shorter, a product of a lower molecular weight is obtained; conversely, if heating is carried out for a longer period, a product of higher molecular weight is obtained. With this high proportion of trimethylolpropane, an increase of the molecular weight above 1800 is not possible because crosslinking to form a water-insoluble resin occurs.

(III)

If the procedure as in Example 1 is applied, but the equivalent amount of 5-sodium sulfethoxyisophthalic acid is used instead of 5-sodium sulfopropoxyisophthalic acid dimethyl ester, a product is obtained which is very similar to that of Example 1 with respect to water solubility and film hardness.

(IV)

If the procedure as in Example 1 is applied, but 111 grams of 5-sodium sulfoisophthalic acid dimethyl ester is used instead of 132.5 grams of 5-sodium sulfopropoxyisophthalic acid dimethyl ester, then a chemically very similar product is obtained, which, however, at an identical molecular weight of 1420 is soluble only colloidally in water, because aromatic sulfo groups are clearly less water-soluble than aliphatically bonded sulfo groups. If the procedure is as described but at the end of the condensation heating at 240°–245° C. is carried out for 2.5 hours, a product with a molecular weight of approximately 1100 is obtained, which produces a clear solution when dissolved in water.

(V)

45 mole % of IPA; 40 mole % of DMT; 15 mole % of SIM; 90 mole % DEG; 10 mole % of polyethylene glycol 600; 10 mole % of TMP.

In the same apparatus as in Example 1, 187 grams of isophthalic acid (99% strength), 194 grams of terephthalic acid dimethyl ester, 111 grams of 5-sodium sulfoisophthalic acid dimethyl ester, 240 grams of diethylene glycol, 150 grams of polyethylene glycol 600, 4 grams of titanium isopropylate and 6 grams of sodium methylate are heated to 150° C. under nitrogen. The temperature in the flask is then increased over a period of 2 hours to 165° C., while stirring well, and in the course of a further 3 hours is increased to 190° C. and finally heating is carried out for a further 4 hours to 220°–225° C. Methanol and water are distilled off in the course of this. The internal temperature is then briefly lowered to 150° C., 33.5 grams of trimethylolpropane are added, then the mixture is heated again under nitrogen for 4 hours to 220°–225° C. Then, at the same temperature, heating is carried out for a further 3 hours using a water jet pump (approximately 12 torr) and finally for a further half hour in a medium-high vacuum of approximately 0.5 torr. In the course of this some more water as well as excess diethylene glycol are distilled off. A highly viscous, amber-colored melt is obtained, which, however, may easily be diluted with warm water to 3800 grams to form a viscous, 20% strength colloidal solution of a molecular weight of approximately 3740. The pH value is 4.8 and can be adjusted to 6.5–7 by stirring in a little sodium hydroxide solution of 25% strength.

(VI)

If in V, 100 grams of polyethylene glycol 400 are used instead of 150 grams of polyethylene glycol 600, a product which is slightly less water-soluble but with otherwise analogous properties is obtained.

(VII)

If in V, 500 grams of polyethylene glycol 2000 are used instead of 150 grams of polyethylene glycol 600, and finally the resulting melt is adjusted to a 20% solids content again, a product of better water-solubility, with otherwise similar properties, is obtained.

(VIII)

90 mole % of IPA; 10 mole % of SIM; 80 mole % of DEG; 20 mole % of 1,6-hexanediol; 40 mole % of trimethylolethane.

In the same apparatus as that in Example 1, 373.5 grams of IPA of a degree of purity of 99%, 74 grams of SIM, 212 grams of DEG, 59 grams of 1,6-hexanediol and 120 grams of trimethylolethane are heated under nitrogen to 170° C. while stirring well, without the addition of a catalyst. In the course of 8 hours, the internal temperature is then increased by 10° C. per hour until 240° C. is reached. Methanol and water distil off in a continuous flow. Finally a vacuum of approximately 12 torr is applied for 2 hours at 240°-245° C. In the course of this 65 grams of a colorless oil distil off, predominantly the diethylene glycol used in excess. 672 grams of a viscous amber-colored residue remain, which may easily be diluted with warm water to 2240 grams to form a light, clear, 30% strength solution. This solution has a pH value of 4.1 and can conveniently be neutralised by stirring with very little strong sodium hydroxide solution. The molecular weight of the polyester is 1270.

(IX)

If 31 grams of ethylene glycol are used in VIII instead of the hexanediol, a product with analogous properties is obtained.

(X)

If, instead of the hexanediol used in VIII, 38 grams of 1,2-propanediol or 1,3-propanediol, 45 grams of 1,4-butanediol, 67 grams of dipropylene glycol, 57 grams of 1,4-cyclohexanediol or 99 grams of or 169 grams of are used, then products are obtained with slightly modified properties with respect to film hardness and elasticity.

(XI)

70 mole % of IPA; 20 mole % of 1,3-cyclohexanedicarboxylic acid; 10 mole % of SIM; 20 mole % of 1,6-hexanediol; 80 mole % of DEG; 40 mole % of glycerin.

In the same experimental arrangement as in Example 1, 290.5 grams of isophthalic acid of 99% strength, 86 grams of 1,3-cyclohexanedicarboxylic acid, 74 grams of 5-sodium sulfoisophthalic acid dimethyl ester, 212 grams of diethylene glycol, 59 grams of 1,4-hexanediol and 92 grams of glycerin, without the addition of a catalyst, are heated over the course of 2 hours, while stirring well, to 170° C. under carbon dioxide, and then the temperature in the flask is increased by 10° C. per hour until a temperature of 240° C. is reached. Then stirring is carried out at 240°-245° C. for a further 1 hour and 20 minutes in a water jet pump vacuum (approximately 12 torr). During the polycondensation reaction methanol, water and finally the excess diethylene glycol distil off. 662 grams of amber-colored polycondensate remain, which on cooling solidifies to a brittle resin and can be pulverised well. It dissolves well in water and is preferably used in the form of an aqueous solution of 30% strength. The apparent molecular weight is 1170. The 30% strength solution has a pH value of 5.4 and can easily be neutralised by stirring in very little strong sodium hydroxide solution.

(XII)

A product similar to that in Example XI, but more readily soluble in water, is obtained if instead of the SIM in Example XI 88.5 grams of 5-sodium sulfonatopropoxyisophthalic acid dimethyl ester are used.

(XIII)

Water-soluble polyesters with similar properties valuable for use in hair cosmetics are also obtained if instead of the cyclohexanedicarboxylic acid in Example XI, an equivalent amount of succinic acid diethyl ester, succinic acid anhydride, maleic acid anhydride, fumaric acid dipropyl ester, glutaric acid or adipic acid is used.

(XIV)

45 mole % of adipic acid; 40 mole % of DMT; 15 mole % of sulfophthalic acid dimethyl ester; 90 mole % of DEG; 10 mole % of polyethylene glycol 600; 5 mole % of pentaerythritol 164.3 grams of adipic acid, 194 grams of DMT, 111 grams of 4-sodium sulfophthalic acid dimethyl ester, 240 grams of diethylene glycol and 150 grams of polyethylene glycol 600, as well as 4 grams of titanium tetraisopropylate and 6 grams of sodium methylate as catalyst mixture, are placed in the same experimental arrangement as that described in Example 1, and heated under nitrogen in the course of 2 hours to 150° C., in the course of a further 2 hours to 165° C., then in the course of 3 hours to 195° C., in the course of one hour to 220° C. and then for a further 4 hours at 220-225° C. Methanol and water distil off during the course of this. Cooling to 150° C. is then carried out and at this temperature 17 grams of pentaerythritol are admixed. Heating under nitrogen is then carried out again for 4 hours to 220-225° C. while stirring well, and finally a vacuum of approximately 10 torr is applied at the same temperature for a further 4 hours and thus the condensation proceeds to completion. 738 grams of a residue remains which may easily be diluted with water to 3700 grams to form a 20% strength colloidal solution. The pH value of this solution is approximately 4.1. The solution can be neutralised with a little 25% strength sodium hydroxide solution by adjusting to a pH value of approximately 6. The apparent molecular weight of the product is 1900.

(XV)

If the Example XIV an equivalent quantity of isophthalic acid dimethyl ester is used instead of DMT, a product of slightly higher elasticity is obtained.

(XVI).

If in Example XIV instead of 4-sodium sulfophthalic acid dimethyl ester an equivalent quantity of 2-sodium sulfotetrephthalic acid dimethyl ester, 5-sodium sulfoisophthalic acid dimethyl ester-N-methyl tauride, 5-sulfopropoxyisophthalic acid dimethyl ester (sodium salt) or 5-sodium sulfoisophthalic acid dimethyl ester is used, products with slightly higher water solubilities are obtained.

(XVII)

70 mole % of IPA; 15 mole % of SPO; 15 mole % of TMSA; 100 mole % of DEG.

In the same experimental apparatus as that described in Example 1, 290.5 grams of isophthalic acid of 99% strength, 132.5 grams of 5-sodium sulfopropoxyisophthalic acid dimethyl ester, 72 grams of trimellitic acid anhydride and 265 grams of diethylene glycol without the addition of a catalyst are heated under nitrogen over the course of one hour to 150° C., in a further 2 hours to 165° C., in a further three hours to 190° C., in one hour to 220° C. and then for three hours at 220–225° C. Methanol and water distil off and the melt becomes increasingly more viscous. Continuous thorough mixing using a vigorous agitator is important. Finally heating at 220–225° C. is carried out for a further 3 hours using a water jet pump at a vacuum of 10–12 mm Hg. 660 grams of an amber-colored residue remain, which may easily be diluted with water to 3300 grams to form a 20% strength, slightly milky solution of a pH of 3.0. It is advantageously neutralised with a little strong sodium hydroxide solution, whereby it becomes completely clear. Any turbidity that might remain can easily be removed by stirring with 1–2% strength diatomaceous earth and pressing through a pressure filter. The apparent molecular weight is 1430.

If the reaction time is correspondingly shortened, particularly during the last hours in vacuo, a low molecular weight product is obtained. If, for example, under otherwise identical conditions heating is carried out for only one hour using a water jet pump the product has a molecular weight of approximately 960.

(XVIII).

70 mole % of IPA; 15 mole % of SIM; 15 mole % of hemimellitic acid; 80 mole % of DEG; 10 mole % of TEG; 10 mole % of 1,6-hexanediol.

In the same experimental apparatus as that described in Example 1, 290.5 grams of 99% strength isophthalic acid, 111 grams of 5-sodium sulfoisophthalic acid dimethyl ester, 78.8 grams of hemi-mellitic acid, 212 grams of diethylene glycol, 37.5 grams of triethylene glycol and 29.5 grams of 1,6-hexanediol with 3 grams of titanium tetraisopropylate as the catalyst are heated under nitrogen as follows: in 1 hour to 150° C., in 2 hours to 165° C., in 3 hours to 190° C., in 1 hour to 220° C. and for 2 hours at 220–225° C. The distilled off mixture consisting of some methanol and water is separated off; the mixture is then heated for a further hour to 220–225° C. in a vacuum of 10–12 torr. 635 grams of a light residue is obtained which is best diluted still warm to 2160 grams with water to form a 30% strength solution. The pH value is only 3.1 so, advntageously, the solution is neutralised with a little strong sodium hydroxide solution. The apparent molecular weight is 1190.

(IXX)

If instead of the 5-sodium sulfoisophthalic acid dimethyl ester used in XVIII an equivalent amount of the methyl tauride is used, a product which dissolves slightly more readily in water is obtained.

(XX).

50 mole % of IPA; 20 mole % of DMT; 10 mole % of SIM; 20 mole % of citric acid; 100 mole % of diethylene glycol.

In the same experimental apparatus as that described in Example 1, 207.5 grams of isophthalic acid, 97 grams of terephthalic acid dimethyl ester, 74 grams of 5-sodium sulfoisophthalic acid dimethyl ester, 96 grams of citric acid, 265 grams of diethylene glycol and 2 grams of titanium tetraisopropylate are heated under nitrogen in one hour to 150° C., then in the course of 2 hours to 165° C., in the course of 3 hours to 190° C., in the course of a further hour to 220° C., then for 2 hours at 220–225° C., and finally for a further half hour in a vacuum of 10–12 torr at 220–225° C.; methanol and water distil off. 590 grams of a brownish residue, which can readily be diluted with water to 1970 grams to form a 30% strength solution of a pH value of 3.1. Since this strong acidity can impair the stability of the aqueous solution, it is advantageously diluted first only to 1870 grams, neutralised with 25% strength sodium hydroxide solution, and then the remaining solvent is added. Any turbidity can be overcome by stirring with 20 grams of diatomaceous earth and pressing through a pressure filter. The molecular weight of this polyester is 1510.

(XXI).

A similar product to that in XX is obtained if instead of the citric acid in XX 20 mole % of tartaric acid are used.

(XXII)

70 mole % of IPA; 10 mole % of MA; 20 mole % of TMSA; 100 mole % of DEG.

In the same experimental apparatus as that described in Example 1, 290 grams of isophthalic acid, 24.5 grams of maleic acid anhydride, 265 grams of diethylene glycol and 0.7 grams of ditert.-butylhydroquinine are heated under nitrogen, while stirring well, in the course of one hour to 160° C., then in the course of a further hour to 180° C., in the following hour to 220° C., in the course of the next hour to 220° C., and then for two hours at 220–225° C. The mixture is then temporarily cooled to 150° C. and at this temperature 96 grams of trimellitic acid anhydride are stirred in, in portions, over a period of half an hour. After this the temperature is increased again, in one hour, to 220° C., and the content of the flask is stirred well for 2 hours at 220–225° C. Then a water jet vacuum of 10–15 torr. is applied and this temperature is maintained for a further half an hour. 598 grams of a viscous, amber-colored residue is obtained, which is allowed to cool, in vacuo, to 100° C. Only then is the vacuum lifted, and nitrogen passed through the apparatus again. A solution of 50 grams of sodium bisulfite in 100 ml of water is then stirred in over the course of one hour (at 100° C.), stirring at 100° C. is then carried out for 3 hours, and finally the product is diluted to 3240 grams with water. A 20% strength almost clear, but still acidic, aqueous solution is obtained, the pH value of which is adjusted to 6.5 with approximately 80 ml of a 25% strength sodium hydroxide solution so as to avoid hydrolysis. The molecular weight of the polycondensate is 1400, measured osmometrically in dimethylformamide as in all determinations.

XXIII

If instead of the maleic acid anhydride used in XXII an equivalent amount of itaconic acid anhydride is used, a product with similar physical properties is obtained.

(XXIV)

If 0.25 mole of diethylene glycol is Example XXII is replaced by an equivalent amount of polyethylene glycol 300, 600 or 1000, products with slightly modified properties, in so far as the hydrophilic property increases with the increase in chain length of the polyglycol ether radical, are obtained.

(XXV)

50 mole % of IPA; 15 mole % of SIM; 15 mole % of MA; 20 mole % of TMSA; 60 mole % of DEG; 40 mole % of 1,4-butanediol.

In the same experimental apparatus as that described in Example 1, 207.5 grams of isophthalic acid, 111 grams of SIM, 37 grams of maleic acid anhydride, 159 grams of diethylene glycol, 90 grams of 1,4-butanediol, 1 gram of titanium isopropylate and 1 gram of ditert.-butylhydroquinone are heated as follows in a nitrogen atmosphere; first of all to 150° C. in one hour, then the temperature is increased by 15° C. per hour until 220° C. is reached, and then the temperature is maintained at 220-225° C. for 4 hours. The temperature is then temporarily lowered to 150° C. and 96 grams of trimellitic acid anhydride are stirred in, in portions, over a period of half an hour (under nitrogen). Then the temperature is raised to 200° C. again, heating is carried out at 200-210° C. for one hour, at 210-220° C. for one hour, and at 220-225° C. for 2 hours, and at this temperature a water jet pump vacuum of 10-15 mm Hg is applied for a further half an hour. The viscous melt is then allowed to cool to 100° C. and an aqueous solution of 75 grams of sodium bisulfite in 150 grams of water is stirred in (under nitrogen) over a period of one hour. Heating at 100° C. for a period of 3 hours is then carried out, the viscous paste is diluted with water to a 20% strength solution and the pH value is adjusted to approximately 6.5 with a 25% strength sodium hydroxide solution. The molecular weight of the slightly colloidal solution is 1550.

XXVI 85 mole % of DMI; 15 mole of K-SIM; 90 mole % of TEG; 20 mole % of trimethylolethane.

In the experimental apparatus described in Example 1, 247.35 grams of isophthalic acid dimethyl ester, 70.2 grams of potassium sulfoisophthalic acid dimethyl ester, 202.5 grams of triethylene glycol 3 grams of titanium isopropylate and 4 grams of potassium methylate are heated in a nitrogen atmosphere to 130° C. in one hour while stirring well, in the course of which methanol begins to distil off. The reaction temperature is then increased by 15° C. per hour until 220° C. is reached. Stirring at 220-225° C. is then carried out under nitrogen for 4 hours, and subsequently for a further 8 hours at a vacuum of 10-15 mm Hg. The internal temperature is then temporarily dropped to 150° C. and at this temperature 36 grams of trimethylolethane are stirred in, in portions, over a period of a quarter of an hour. Then heating under nitrogen to 210-215° C. is carried out in 4 hours, and finally a vacuum of 10-15 mm Hg is applied at this temperature for a further hour. A very viscous melt is obtained which may be diluted with water to form a 20% strength solution rendered slightly turbid colloidally. The molecular weight of the polycondensate so obtained is 2200.

XXVII

If instead of 202.5 grams of triethylene glycol in XXVI only 122.5 grams are used (=0.75 mole) and also 53.1 grams of 1,6-hexanediol (=0.45 mole) and 90 grams of polyethylene glycol 600 (=0.15 mole), a clearly more viscous polycondensate is obtained.

(XXVIII)

50 mole % of DMI; 30 mole % of DMT; 20 mole % of the sodium salt of 1,2,4-benzenetricarboxylic acid methyl ester-5-sulfonic acid; 110 mole % of DEG.

In the apparatus described in Example 1, 145.5 grams of isophthalic acid dimethyl ester, 87.3 grams of terephthalic acid dimethyl ester, 106.2 grams of the sodium salt of 1,2,4-benzenetricarboxylic acid methyl ester-5-sulfonic acid, 174.9 grams of diethylene glycol and 3 grams of titanium tetraisopropylate are heated under nitrogen to 150° C. in the course of one hour. The reaction temperature is then increased by 15° C. per hour. Methanol distils off. Heating for a further 2 hours at 205-210° C. is then carried out, and finally, a water jet vacuum of approximately 12 mm Hg is applied for 15-30 minutes, until the content of the flask takes on a highly-viscous consistency. The product is then cooled to 120° C. and diluted with water to form a solution of 20% strength. This solution is water clear and thinly liquid. It has a pH value of approximately 4.5 which is adjusted to 6.0-6.5 by adding a few drops of 25% strength sodium hydroxide solution. The molecular weight of this polycondensate, measured osmometrically in dimethyl formamide, is between 1300 and 1400.

What is claimed is:

1. Hair-treatment agents having a content of branched copolyesters dispersible or soluble in water and an apparent molecular weight of 600 to 5000, and having a content of SO$_3$M groups, wherein M represents an alkali metal ion or ammonium ion or the cationic radical of an organic amine, the copolyesters being made up of the radical of the following formulae:

(A₁)

—O—R₂—O— (B)

—O—R'₂—O— (B₁)

in which:
- R₁ represents a direct bond or a divalent aliphatic, cycloalphatic or aromatic radical which may also contain an SO₃M group,
- m represents the number 0, 1 or 2,
- R₁' represents an aliphatic, cycloaliphatic or aromatic radical, which may also contain an SO₃M group, and which when m=0 is trivalent, when m=1 is tetravalent and when m=2 is pentavalent,
- R₂ represents a divalent aliphatic, cycloaliphatic or araliphatic radical, which may also contain an SO₃M group,
- n represents the number 0, 1 or 2,
- R₂' represents an aliphatic or cycloaliphatic radical which when n=0 is trivalent, when n=1 is tetravalent and when n=2 is pentavalent and may also contain an SO₃M group.

2. Hair-treatment agents according to claim 1, wherein the alkali metal ion is a sodium ion.

3. Hair-treatment agents according to claim 1 wherein the organic amine is a trimethylamine, triethylamine or triethanolamine.

4. Hair-treatment agents according to claim 1, wherein the copolyesters contain 5 to 40 mole % of SO₃M groups calculated on the di- and/or polycarboxylic acids used to produce the polyester.

5. Hair-treatment agents according to claim 1, wherein the copolyesters contain 10 to 30 mole % of SO₃M groups calculated on the di- and/or polycarboxylic acids used to produce the polyester.

6. Hair-treatment agents according to claim 1, wherein m represents the number 0 or 1.

7. Hair-treatment agents according to claim 6, wherein n represents the number 0 or 1.

8. Hair-treatment agents according to claim 1, wherein the copolyester contains 80 to 140 mole % of radicals (B+B₁) calculated on 100 mole % of the radicals (A+A₁).

9. Hair-treatment agents according to claim 1, wherein the copolyester contains 1 to 40% of branching radicals (A₁+B₁) calculated on 100 mole % of the radicals (A+A₁).

10. Hair-treatment agents according to claim 1, wherein the copolyester contains 5 to 40 mole % of the radicals (A₁+B₁) calculated on 100 mole % of the radicals (A+A₁).

11. Hair-treatment agents according to claim 1, wherein at least 40 mole % of the radicals A in the copolyester are radicals of the formula (A₂)

which may also contain an SO₃M group.

12. Hair-treatment agents according to claim 1, wherein at least 40 mole % of the radicals A in the copolyester are radicals of the formula (A₃)

which may also contain an SO₃ M group.

13. Hair-treatment agents according to claim 1, wherein at least 40 mole % of the radicals (B+B₁) in the copolyester are radicals of the formula

—O—CH₂CH₂OCH₂CH₂O— and/or

—O—CH₂CH₂OCH₂CH₂OCH₂CH₂O—

14. Hair-treatment agents according to claim 1, wherein an equivalent portion of the radicals A and B in the copolyester is replaced by radicals of the formula (C)

in which
- R₃ represents a divalent, aliphatic, cycloaliphatic or araliphatic radical, which may also contain an SO₃M group.

15. Hair-treatment agents according to claim 1, wherein an equivalent portion of the radicals A₁ and B₁ in the copolyester is replaced by radicals of the formula in which p and q represent the numbers 0, 1, 2 or 3 and p and q are so selected that p+q=1, 2 or 3 and R₃' represents an aliphatic radical which may also carry an SO₃M group.

16. Hair-treatment agents according to claim 1, wherein p and q are so selected that (p+q)=1 or 2.

17. Hair-treatment agents according to claim 1, wherein in the copolyester, R₂ represents a divalent aliphatic radical having 2 to 10 carbon atoms, a divalent aliphatic radical having a molecular weight of up to 2000 and interrupted by ether bridges, wherein 2 to 10 carbon atoms are present between two ether bridges or oxygen atoms, a divalent radical of a polyethylene glycol of a molecular weight of 300 to 2000 or an ethylene propylene polyglycol of a molecular weight of 300 to 2000, a divalent cycloaliphatic radical having 6 to 10 carbon atoms or a divalent araliphatic radical having 8 to 14 carbon atoms.

18. Hair-treatment agents according to claim 1, wherein in the copolyester, $R_1$ represents a divalent aliphatic radical having 2 to 8 carbon atoms, a divalent cycloaliphatic radical having 6 to 8 carbon atoms or a divalent aromatic radical having 6 to 12 carbon atoms.

19. Hair-treatment agents according to claim 1, wherein in the copolyester, $R_3$ represents a divalent aliphatic radical having 1 to 10 carbon atoms, a divalent cycloaliphatic radical having 6 to 11 carbon atoms or a divalent araliphatic radical having 8 to 12 carbon atoms.

20. Hair-treatment agents according to claim 1, wherein in the copolyester, $R_1'$ represents an aliphatic radical having 2 to 5 carbon atoms, a cycloaliphatic radical having 6 to 8 carbon atoms, or an aromatic radical having 6 to 12 carbon atoms.

21. Hair-treatment agents according to claim 1, wherein in the copolyester, $R_2'$ represents an aliphatic radical having 3 to 12 carbon atoms or a cycloaliphatic radical having 6 to 8 carbon atoms.

22. Hair-treatment agents according to claim 1, wherein in the copolyester, $R_3'$ represents an aliphatic radical having 2 to 8 carbon atoms.

23. Hair-treatment agents according to claim 1, wherein they have a content of 0.1 to 10, preferably 0.5 to 4% of the copolyester used in accordance with the invention, calculated on the total weight of the hair-treatment agent.

* * * * *